US00PP15714P3

(12) United States Plant Patent
Redman

(10) Patent No.: US PP15,714 P3
(45) Date of Patent: Apr. 12, 2005

(54) ***CHRYSANTHEMUM* PLANT NAMED 'CHISEL TIME CERISE'**

(50) Latin Name: *Chrysanthemum morifolium*
Varietal Denomination: Chisel Time Cerise

(75) Inventor: Ruth Redman, Bognor Regis (GB)

(73) Assignee: Cleangro LTD (GB)

( * ) Notice: Subject to any disclaimer, the term of this patent is extended or adjusted under 35 U.S.C. 154(b) by 247 days.

(21) Appl. No.: 10/652,193

(22) Filed: Aug. 29, 2003

(65) Prior Publication Data

US 2005/0050604 P1 Mar. 3, 2005

(51) Int. Cl.[7] ..... A01H 5/00

(52) U.S. Cl. ..... Plt./286

(58) Field of Search ..... Plt./286, 298

*Primary Examiner*—Anne Marie Grunberg
*Assistant Examiner*—June Hwu
(74) *Attorney, Agent, or Firm*—Howrey Simon Arnold & White, LLP

(57) ABSTRACT

A new variety of pot *Chrysanthemum* plant named 'Chisel Time Cerise,' having a good uniform canopy of cerise pink spoon tip single flowers. The new variety has a medium tall vigor, free branching, uniform spreading habit and good foliage presentation.

1 Drawing Sheet

Latin name of the genus and species: Botanical classification: *Chrysanthemum morifolium.*

Variety denomination: The new *Chrysanthemum* variety denomination is 'Chisel Time Cerise.'

BACKGROUND OF THE INVENTION

The present invention comprises a new and distinct cultivar of *Chrysanthemum* botanically known as *Chrysanthemum morifolium,* and referred to by the cultivar name 'Chisel Time Cerise.'

'Chisel Time Cerise,' identified as 21033-6, discovered in Chischester, West Sussex, United Kingdom as a whole plant mutation found in a controlled cultivated planting of the variety 'Chisel Time Pink' (U.S. Plant patent application Ser. No. 10/364,251).

The new variety 'Chisel Time Cerise' has been asexually reproduced by vegetative cuttings in Chichester, West Sussex, United Kingdom and the distinguishing characteristics are retained through successive generations of asexual reproduction.

BRIEF SUMMARY OF THE INVENTION

'Chisel Time Cerise' is a pot type of *Chrysanthemum* plant variety having golden quills with pink spoon tip single flowers.

Comparison with Parent

Plants of the new *Chrysanthemum* variety 'Chisel Time Cerise' are similar to the parent cultivar Chisel Time Pink in plant habitat and growth rate. In side-by-side comparisons in Chichester, West Sussex, United Kingdom, under commercial practice, plants of the new *Chrysanthemum* variety 'Chisel Time Cerise' differed from plants of the parent cultivar Chisel Time Pink in the following characteristics.

1. The new variety 'Chisel Time Cerise' produces golden quills with cerise spoon tip single flowers whereas the parent cultivar Chisel Time Pink produces silver quills with pink spoon tip single flowers.

Comparison with Other Varieties

Plants of the new *Chrysanthemum* variety 'Chisel Time Cerise' are similar to the cultivar 'Scott' (U.S. Plant Pat. No. 14,155) in plant habitat and growth rate.

However, in side-by-side comparisons in Chichester, West Sussex, United Kingdom, under commercial practice, plants of the new *Chrysanthemum* variety 'Chisel Time Cerise' differed from plants of the cultivar Scott in the following characteristics.

1. The new variety 'Chisel Time Cerise' produces golden quill with cerise spoon tip single flowers whereas the cultivar Scott produces light pink quill with dark pink spoon tip single flowers.
2. Plants of the new variety 'Chisel Time Cerise' have larger and taller inflorescence than plants of the cultivar Scott.
3. The new variety 'Chisel Time Cerise' has a quicker response time than the plants of the cultivar 'Scott.'

BRIEF DESCRIPTION OF ILLUSTRATION

Typical specimens of the plant and flowers for the new *Chrysanthemum* variety 'Chisel Time Cerise' are shown in the accompanying digital photograph. The colors shown are as true as possible within the usual limits of this kind of illustration.

FIG. 1 is a whole plant view of the new variety 'Chisel Time Cerise' grown in a pot. The plant shown in the illustration is 50 days from the commencement of Short Days.

DETAILED BOTANICAL DESCRIPTION

The following description of the new *Chrysanthemum* variety 'Chisel Time Cerise' is of plants grown in a greenhouse in Chichester, West Sussex, United Kingdom in the month of July. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5,000 to 6,000 foot candles. The plants respond well to the use of growth retardant, such as one B9 treatment at about 2 gm per liter. To produce a commercial product the plants may be pinched once with the center bud removed. The typical container size for commercial growth is 1 liter. It has been observed that the shelf life of the new variety is about 28 days with a response time of about 7 weeks. The new variety is suitable for growth in a temperature range of 15° C. to 25° C.

The new variety may be produced as a spray. The following description is with respect to a plant produced as pot. In the description of this new *Chrysanthemum* variety, color values have been taken from The Royal Horticultural Society Colour Chart (R.H.S.C.C.).

Plant

Plant type: Pot.
Habit: Upright.
Height: 22 cm.
Width: 30 cm.
Branching characteristics: Upright and spreading.
Length of lateral branches: 16 cm.
Number of breaks from pinch: 5.
Stem color: 137C.
Response time: 49 days.
Vigor: Medium Tall.
Shelf life: 28 days.
Disease (susceptibility or resistance): None observed.
Pest (susceptibility or resistance): None observed.
Drought or temperature resistance: None observed.
Growth retardant type and treatment: 3 applications of 2.5 gm/liter B9 @2, 21 and 28 days after sticking of unrooted cuttings.

The plants were grown for 2 weeks in Long Day conditions (20 hours of light) and then transferred to Short Day conditions (13 hours of dark).

Propagation:
*Type.*—Vegetative propagation via stem cuttings.
*Time to rooting.*—14 days with soil temperatures of 18° C.
*Rooting habit.*—After 7 days the first roots emerge and form root primordia. In 14 Long Days a complete root system is developed.

Foliage

Number of leaves per lateral branch: 10.
Compound or single: Single.
Arrangement of leaves: Alternate.
*Shape of leaf.*—Typically 5 lobed.
*Size of leaf.*—Width (cm): 5.5. Length (cm): 8.5.
*Leaf apex.*—Acute.
*Base.*—Obtuse.
*Attachment.*—Petioled.
*Aspect.*—Slight undulating.
*Margin.*—Palmately lobed.
*Surface characteristics.*—Top: slightly pubescent. Bottom: Pubescent.
Petiole:
*Color.*—137D.
*Length.*—1.5 cm.
Venation: Net, prominent mid vein at underside.
*Color.*—Upper side: near 137D. Under side: Near 138B.
Color:
*Mature leaf, upper side.*—Near 137A; under side: near 137D.
*Young leaf, upper side.*—Near 137C; under side: near 137D.

Flower

Flower appearance: Matte.
Flower type: Single.
Flower form: Cupped.
Flower shape: Round.
Flowering habit: Cyme.
Number of blossoms per branch: 6 to 7.
Inflorescence form: Cyme.
*Depth of fully expanded blossoms.*—2 cm.
*Diameter of fully expanded blossoms.*—8 cm.
Phyllaries:
*Number.*—25.
*Color.*—Near 137D.
*Length.*—0.7 cm.
*Width.*—0.2 cm.
*Texture/appearance.*—Pubescent.
Peduncle:
*Length.*—10 cm (average).
*Color.*—Near 137D.
*Surface.*—Pubescent.
*Habit.*—Slightly undulating.
*Strength.*—Medium.
Pedicel:
*Length.*—Terminal: 2 cm; lateral: 3 cm.
*Color.*—Near 137D.
*Surface.*—Pubescent.
*Habit.*—Slightly undulating.
*Strength.*—Medium.
Ray florets:
*Form/shape.*—Straight and cylindrical.
*Texture/appearance.*—Matte.
*Number per flower.*—38.
*Tube and spoon length.*—3.5 cm Tube width: 0.2 cm.
*Spoon length.*—0.5 cm Spoon width: 0.4 cm.
*Apex.*—Rounded.
*Base.*—Tapered.
*Margin.*—Entire.
Disc florets:
*Form/shape.*—Cylindric.
*Texture/appearance.*—Shiny.
*Number per flower.*—135.
*Length.*—0.6 cm; Width: 0.1 cm.
*Diameter of disc.*—1.6 cm.
Fragrance: None observed.
Flower bud (at onset of color):
*Length.*—1.5 cm.
*Diameter.*—1.2 cm.
*Form/shape.*—Spherical.

General flower color:

1. *Ray florets, upper side.*—Immature: near 57B. Mature: near 58B. Older/Fading: near 58C.
2. *Ray florets, under side.*—Immature: near 58B. Mature: near 58B. Older/Fading: near 58C.
3. *Disc florets.*—Immature: near 144A. Mature: near 144C. Older/Fading: near 151D.
4. *Bud.*—57B.
5. *Ray florets, outer tube.*—Near 18B.

Flower progression with age: There is no change with the flower form, but there is a slight color fading with age. Lastingness of the bloom is about 28 days.

Reproductive Organs

Gynoecium: present on ray and disc florets.

*Pistil number on ray florets.*—38.

*Pistil number on disc florets.*—135.

*Stigma color.*—154A.

*Stigma shape.*—Forked.

*Style color.*—154B.

*Style length on ray florets.*—0.4 cm.

*Style length on disc florets.*—0.4 cm.

Androecium present on disc florets only:

*Stamen number.*—25–40.

*Anther shape.*—Clubbed.

*Anther color.*—Near 14C.

*Pollen color.*—Near 12A.

*Pollen quantity.*—Medium.

Fruit and seeds: None observed.

What is claimed is:

1. A new and distinct variety of *Chrysanthemum* plant, substantially as described and illustrated herein.

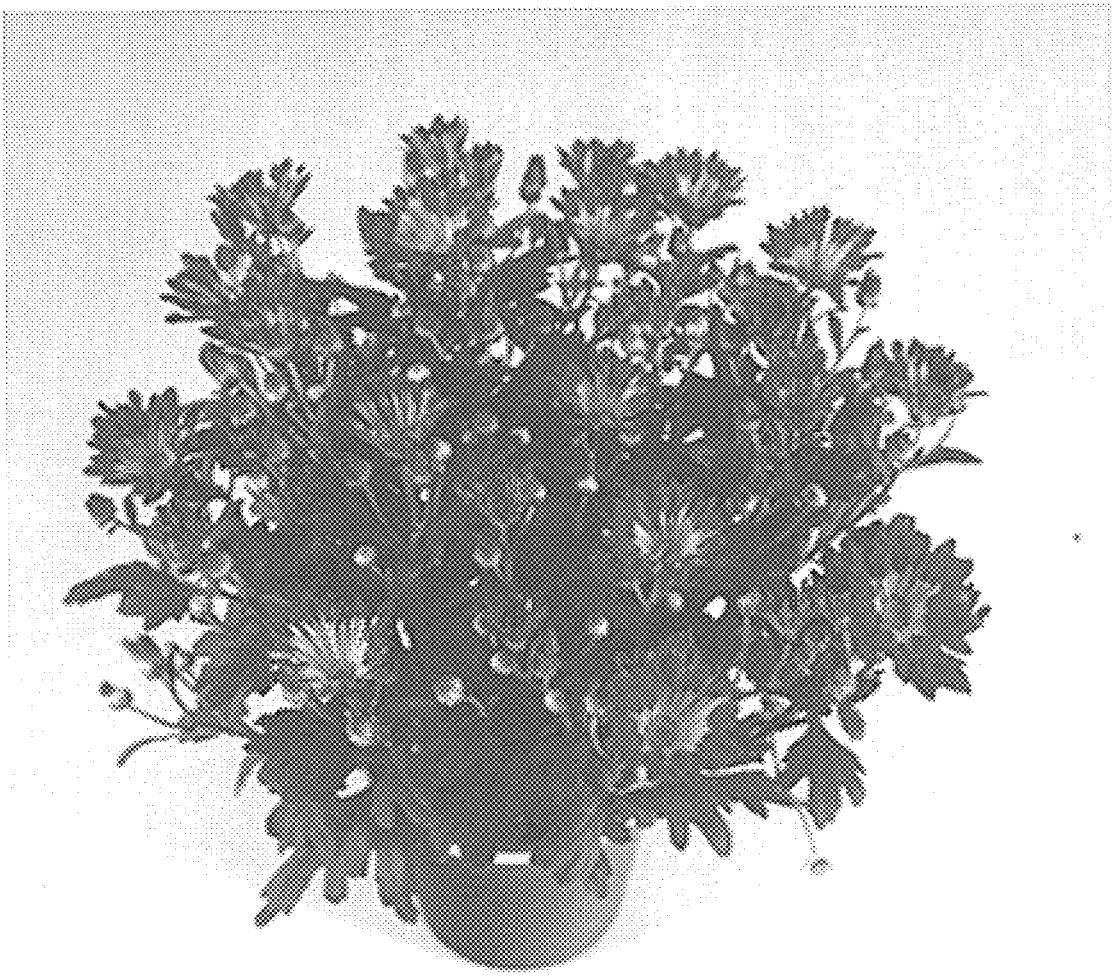

* * * * *